United States Patent [19]

Coenen et al.

[11] Patent Number: 4,898,990
[45] Date of Patent: Feb. 6, 1990

[54] PROCESS FOR THE EXTRACTION OF VANILLIN

[75] Inventors: Hubert Coenen, Essen; Reinhard Konrad, Bochum, both of Fed. Rep. of Germany

[73] Assignee: Fried. Krupp GmbH, Fed. Rep. of Germany

[21] Appl. No.: 289,516

[22] Filed: Dec. 27, 1988

Related U.S. Application Data

[63] Continuation of Ser. No. 57,895, filed as PCT EP86/00526 on Sep. 12, 1986, published as WO87/01695 on Mar. 26, 1987, abandoned.

[30] Foreign Application Priority Data

Sep. 20, 1985 [DE] Fed. Rep. of Germany ....... 3533562

[51] Int. Cl.$^4$ .................................................. C07C 45/90
[52] U.S. Cl. ..................................................... 568/438
[58] Field of Search ......................................... 568/438

[56] References Cited

U.S. PATENT DOCUMENTS

| | | | |
|---|---|---|---|
| 2,069,815 | 1/1937 | Hibbert | 260/137 |
| 2,544,562 | 3/1951 | Michael | 568/438 |
| 4,021,493 | 5/1977 | Major | 568/468 |
| 4,474,994 | 10/1984 | Makin | 568/438 |

FOREIGN PATENT DOCUMENTS

| | | |
|---|---|---|
| 1493190 | 4/1973 | Fed. Rep. of Germany . |
| 2578246 | 9/1986 | France . |
| 1057911 | 2/1967 | United Kingdom . |
| 0001695 | 3/1987 | World Int. Prop. O. .......... 568/438 |

*Primary Examiner*—Werren B. Lone
*Attorney, Agent, or Firm*—Sughrue, Mion, Zinn, Macpeak & Seas

[57] ABSTRACT

A process for the extraction of vanillin by means of the extraction from a vanillin-containing, water-containing, liquid mixture of substances with carbon dioxide at a temperature of 0° to 110° C. as well as a pressure of 30 to 400 bar and a subsequent separation of vanillin is described. It is contemplated that with this process the vanillin-containing carbon dioxide is passed through an aqueous hydrogen sulfite- or sulfite-solution at the extraction temperature and the extraction pressure, that this solution is subsequently acidified with sulfuric acid to a pH value of 2 to 4, and that the vanillin-free carbon dioxide is fed back into the extraction stage.

7 Claims, 1 Drawing Sheet

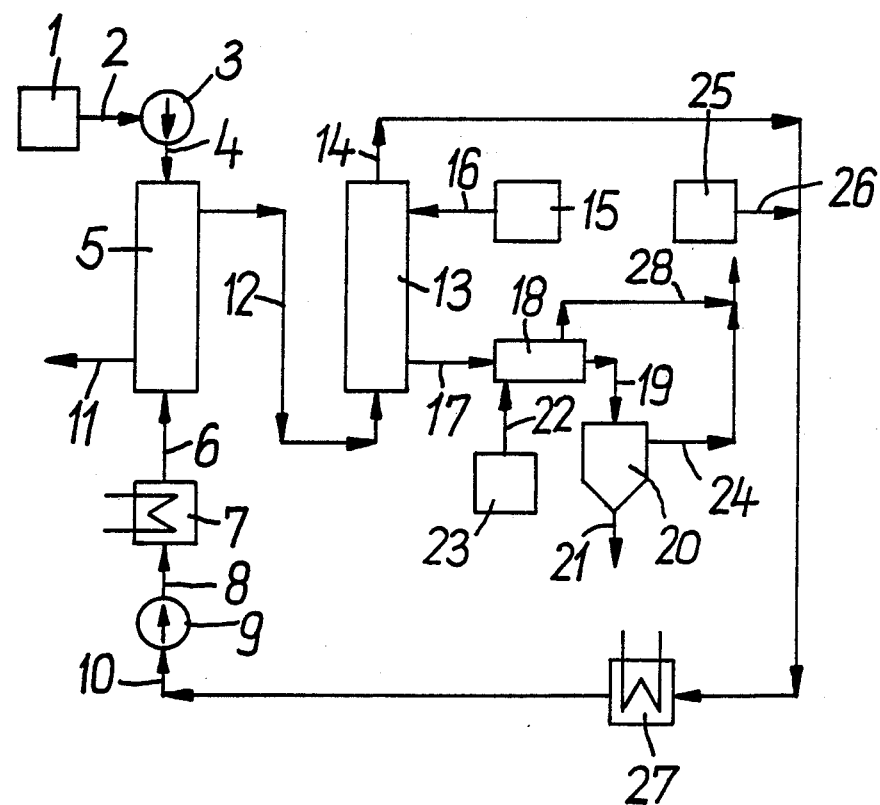

PROCESS FOR THE EXTRACTION OF VANILLIN

This is a continuation of application Ser. No. 07/057,895, filed as PCT EP86/00526 on Sep. 12, 1986, published as WO87/01695 on Mar. 26, 1987, now abandoned.

The invention has to do with a process for the extraction of vanillin by means of extraction from a vanillin-containing, water-containing, liquid mixture of substances with carbon dioxide at a temperature of 0 to 110° C. as well as a pressure of 30 to 400 bar and subsequent separation of the vanillin from the vanillin-containing carbon dioxide.

Vanillin (3-methoxy-4-hydroxy-benzaldehyde) forms colorless needle-shaped crystals with a melting point of 82° C. and is used as an aroma as well as a scent substance. Vanillin is produced by means of a chemical synthesis from eugenol or guajacol or is extracted from the oxidized sulfite waste liquors from wood pulping. In wood pulping, which serves in the recovery of chemical pulp, wood chips are cooked under pressure with a solution of $NaHSO_3$, $Mg(HSO_3)_2$, or $Ca(HSO_3)_2$, whereby the lining is dissolved and is carried off with the sulfite waste liquor. During oxidation of this waste liquor with nitrobenzene in an alkaline medium under pressure or with an oxygen-containing gas in the presence of an oxygen catalyst, vanillin, among others, is formed, which can then be extracted by means of n-butanol or toluene.

From DE-AS 1 493 190, a process is known for the separation of liquid and/or solid mixtures of substances which contain organic compounds and/or compounds having organic groups. In this known process, the substance mixture is treated, with a gas existing under supercritical conditions of temperature and pressure in the temperature range of up to 100° C. over its critical temperature, and after separation of the charged supercritical gas phase the compounds contained in it are reclaimed by means of lowering the pressure and/or raising the temperature. Carbon dioxide can also be utilized as a gaseous extraction agent. If this known process for extracting vanillin from vanillin-containing, liquid substance mixtures is employed, then the disadvantage occurs that during the separation of the vanillin by means of lowering the pressure and/or raising the temperature the other concurrently extracted organic compounds are also partially separated, whereby the vanillin is so strongly contaminated as to be worthless. Moreover, the known process can be run only discontinuously which is detrimental to the economic profitability of the process.

Therefore, the invention is based upon the problem of providing a process for extraction of vanillin which makes it possible continuously to separate vanillin in greatly purer form from vanillin-containing, water-containing, liquid substance mixtures through extraction using carbon dioxide.

The problem lying at the basis of the invention is solved by the fact that vanillin-containing carbon dioxide that is developed during the extraction is passed at the extraction temperature and the extraction pressure through an aqueous $NaHSO_3$, $KHSO_3$, $Na_2SO_3$, or $K_2SO_3$ solution, that the vanillin-containing $NaHSO_3$, $KHSO_3$, $Na_2SO_3$, or $K_2SO_3$ solution is subsequently acidified with sulfuric acid to a pH value of 2 to 4, and that the vanillin-free carbon dioxide is fed back into the extraction stage. It has been demonstrated that the vanillnn of the aforementioned hydrogen sulfite- or sulfite-solutions, almost selectively derived out of the vanillin-containing carbon dioxide phase, is separated off and therefore obtained in a very pure form. The end product has a vanillin content of 90 to 95%. Moreover, the separation of the vanillin takes place under the extraction conditions of temperature and pressure by means of which surprising advantages occur. As the extraction and the separation of the vanillin take place under isotherm and isobar conditions, continuous operation of the process for vanillin extraction is made possible, by means of which the process now for the first time can be economically applied in practice. Although it is known in and of itself that aldehydes in an aqueous phase with the hydrogen sulfite ion according to the equation

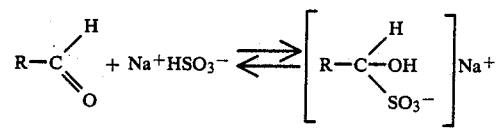

form adducts, which turn out mostly as good crystallizing and hard to dissolve sodium salts, it was surprising that the vanillin can be washed out of a liquid or supercritical vanillin-containing carbon dioxide phase in a mostly selective and mostly quantitative manner with an $NaHSO_3$, $KHSO_3$, $Na_2SO_3$, or $K_2SO_3$ solution. During the use of an $Na_2SO_3$ or $K_2SO_3$ solution the hydrogen sulfite ion is formed according to the equation

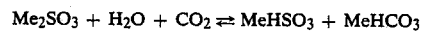

Me = Na, K

The process according to the invention can be conducted particularly successfully when the vanillin-containing carbon dioxide in the aqueous $NaHSO_2$, $KHSO_3$, $Na_2SO_3$, or $K_2SO_3$ solution has a hold time of 0.1 to 3 minutes. With this hold time the vanillin is nearly quantitatively adsorbed in the hydrogen sulfite- or sulfite-solution, whereby, it is especially advantageous that the vanillin-hydrogen sulfite adduct has a good solubility in water.

The separation of the vanillin from the hydrogen sulfite- or sulfite-solution happens in a short time nearly quantitatively if the vanillin-containing $NaHSO_3$, $KHSO_3$, $Na_2SO_3$, or $K_2SO_3$ solution is heated to a temperature of 50 to 90° C. during or after the acidification with sulfuric acid. By warming the solution during or after the acidification, the vanillin falls out in the form of filterable crystals or small droplets of liquid, whereby the liquid droplets likewise crystallize well following appropriate cooling off.

Surprisingly, it has been shown that the process according to the invention can be carried out particularly successfully when as the vanillin-containing, water-containing, liquid substance mixture the oxidized waste liquor from the sulfite wood pulping is utilized. In this manner, the vanillin, which is contained in the oxidized waste liquors from the fabrication of the sulfite chemical pulp, can be recovered at a high level of purity and at a justifiable cost. Moreover, the sulfur dioxide that is developed with the process according to the invention can be used in an advantageous manner to produce the liquor which is needed for the sulfite wood pulping.

The subject matter of the invention will be elucidated in more detail in view of the following illustration and an embodiment example.

The flow chart for the process according to the invention is represented in the illustration. In supply tank 1 is found the oxidized sulfite waste liquor from the wood pulping which contains 0.2 to 2% vanillin. The oxidized sulfite liquor passes by way of pipe 2 into pump 3 where the waste liquor is brought to the extraction pressure. The sulfite waste liquor is subsequently fed by way of pipe 4 on the top side into the extraction column 5, where it is treated with carbon dioxide in countercurrent at a temperature of 0 to 110° C. and at a pressure of 30 to 400 bar. In the process the carbon dioxide becomes charged with vanillin while the nearly vanillin-free sulfite waste liquor is carried off by way of pipe 11. The vanillin-free sulfite waste liquor becomes vaporized, and the residue thereby developed is burned.

The vanillin-containing carbon dioxide passes by way of pipe 12 into the gas scrubber 13, which is charged with an aqueous solution of $NaHSO_3$, $KHSO_3$, $Na_2SO_3$ or $K_2SO_3$. The gas scrubber 13 is operated according to the countercurrent principle. The hydrogen sulfite- or sulfite-solution draws the vanillin from the vanillin-containing carbon dioxide. In order to have to work with the smallest possible flows of mass, and to avoid problems of having to further concentrate, the most concentrated hydrogen sulfite or sulfite solutions possible are utilized that pass from the supply tank 15 through pipe 16 and into the gas scrubber 13. The gas scrubber 13 and the extraction column 5 are operated at the same temperature and the same pressure.

The vanillin-free carbon dioxide passes through pipe 14 into the heat exchanger 27, where it is reduced into a liquid state. Carbon dioxide losses are made up in that carbon dioxide is fed into pipe 14 from the supply tank 25 by way of pipe 26. One can forego the separation of the organic impurities which are extracted in the extraction column 5 together with the vanillin and not washed out of the carbon dioxide in the gas scrubber 13, since the carbon dioxide fed into the circulation in the second pass through the extraction column 5 takes up no more impurities, because when extraction conditions remain the same a saturation of the carbon dioxide with the organic impurities rapidly takes place. The liquidized carbon dioxide passes through pipe 10 into the pumps 9, where adjustment of the extraction pressure occurs. The carbon dioxide is subsequently advanced by way of pipe 8 into the heat exchanger 7 for the setting of the extraction temperature, and it then moves by way of pipe 6 into the extraction column 5.

The vanillin-containing $NaHSO_3$, $KHSO_3$, $Na_2SO_3$ or $K_2SO_3$ solution is removed from the gas scrubber 13 by way of pipe 17 and acidified in the mixing segment 18 with diluted sulfuric acid to a pH value of 2 to 4. At the same time, the acidified solution in the mixing segment 18 is heated to a temperature of about 60° C. The heated solution passes by way of pipe 19 into the settling tank 20, on whose bottom the crystalline vanillin is precipitated, which is withdrawn in discontinuous fashion through pipe 21 and is subsequently dried. In the settling tank 20 and in the mixing segment 18, through the acidifying, the vanillin-containing solution is freed of sulfur dioxide which is carried off through pipes 24 and 28 and is utilized for the production of the sulfite liquor. The sulfuric acid used in the acidification passes out of the supply tank 23 and into the mixing segment 18 by way of pipe 22.

Carbon dioxide is also liberated during the acidification of the vanillin-containing hydrogen sulfite or sulfite solution; the carbon dioxide does not have to be separated from the liberated sulfur dioxide. EMBODIMENT EXAMPLE An oxidized sulfite waste liquor with a pH value of 5.6 and a vanillin content of 6 g/kg of waste liquor was extracted with carbon dioxide for 5 hours during continuous operation of the process. The extraction column 5 was supplied with 0.95 kg of oxidized sulfite waste liquor per hour, which were extracted at 4.65 kg of $CO_2$/hour at 100 bar and 27° C. The vanillin-containing carbon dioxide phase was fed at 100 bar and 27° C. through a frit in 400 ml of an $Na_2SO_3$ solution which contained 75 g of $Na_2SO_3$/l of water. After five hours the entire vanillin-containing $Na_2SO_3$ solution was acidified with sulfuric acid to a pH value of 3.5 and heated to a temperature of 50° C. Thereby, 26 g of vanillin crystallized out, which had a melting point of 74 to 78° C. and a purity of 91.3%. The yield of vanillin amounted to 91%, and the vanillin had the following composition:

| Vanillin | 91.32% |
|---|---|
| Guajacol | 0.02% |
| Acetoguajacol | 8.2% |
| Serine aldehyde | 0.08% |

For the extraction of the vanillin, 0.5 to 10 kg of $CO_2$/kg of waste liquor, according to the portion of the oxidized sulfite waste liquor, are required. The vanillin-$HSO_3$ adduct is very easily dissolved in water and also does not crystallize out in a concentrated hydrogen sulfite- or sulfite-solution. The adduct can therefore be directly recovered by means of the acidification of the vanillin-containing hydrogen sulfite- or sulfite-solution.

The hydrogen sulfites and sulfites utilized in carrying out the process according to the invention have at 30° C. the following solubility, where the hydrogen sulfite is used as pyrosulfite, as the hydrogen sulfites are not stable in solid form.

| 1.1 Mol $Na_2SO_3.7H_2O$/l = | 249 g $Na_2SO_3.7H_2O$/l |
|---|---|
| 2.1 Mol $Na_2S_2O_5$/l = | 406 g $Na_2S_2O_5$/l |
| 3.3 Mol $K_2SO_3$/l = | 518 g $K_2SO_3$/l |
| 1.6 Mol $K_2S_2O_5$/l = | 344 g $K_2S_2O_5$/l |

In order to avoid during the acidification of the vanillin-containing hydrogen sulfite- and sulfite-solutions with sulfuric acid the development of insoluble sulfates, which contaminate the vanillin, one cannot always work with saturated hydrogen sulfite- and sulfite-solutions during acidification, for the sulfates have a solubility different from that of the hydrogen sulfites and sulfites, and moreover, the solubilities are temperature-dependent. For that reason, depending on the temperature which prevails during acidification, one only works with a maximal hydrogen sulfite- and sulfite-concentration in the aqueous solution. At 30° C., this maximal concentration amounts to 248 g $Na_2SO_3 \cdot 7H_2O$/l
406 g $Na_2S_2O_5$/l
117 g $K_2SO_3$/l
164 g $K_2S_2O_5$/l

We claim

1. Process for the extraction of vanillin by means of extraction from a vanillin-containing, water-containing, liquid mixture of substances with carbon dioxide at a temperature of 0 to 110? C. as well as a pressure of 30 to 400 bar and subsequent separation of the vanillin from the vanillin-containing carbon dioxide, comprising: passing the vanillin-containing carbon dioxide at the extraction temperature and the extraction pressure through an aqueous $NaHSO_3$, $KHSO_3$, $Na_2SO_3$, or $K_2SO_3$ solution to separate the vanillin from the carbon dioxide and form a vanillin-containing aqueous $NaHSO_3$, $KHSO_3$, $Na_2SO_3$ or $K_2SO_3$ solution and a vanillin-free carbon dioxide, subsequently acidifying the vanillin-containing $NaHSO_3$, $KHSO_3$, $Na_2SO_3$ or $K_2SO_3$ solution with sulfuric acid to a pH value of 2 to 4, and feeding the vanillin-free carbon dioxide back into the extraction stage.

2. Process according to claim 1, wherein the vanillin-containing carbon dioxide is held for a time of 0.1 to 3 minutes in the aqueous $NaHSO_3$, $KHSO_3$, $Na_2SO_3$ or $K_2SO_3$ solution.

3. Process according to claim 1 wherein the vanillin-containing $NaHSO_3$, $KHSO_3$, $Na_2SO_3$ or $K_2SO_3$ solution, during and after acidification with the sulfuric acid, is heated to a temperature of 50 to 90? C.

4. Process according to claim 1, wherein the vanillin-containing, water-containing, liquid mixture of substances is oxidized sulfite waste liquor from wood pulping.

5. Process according to claim 1, wherein the vanillin-containing, water-containing, liquid mixture of substances has a vanillin content of 0.2 to 2% by weight.

6. Process according to claim 4, wherein the vanillin-containing, water-containing, liquid mixture of substances has a vanillin content of 0.2 to 2% by weight.

7. Process according to claim 2, wherein the vanillin-containing $NaHSO_3$, $KHSO_3$, $Na_2SO_3$ or $K_2SO_3$ solution, during and after acidification with the sulfuric acid, is heated to a temperature of 50 to 90? C.

* * * * *